United States Patent [19]

Woo

[11] 4,256,859

[45] Mar. 17, 1981

[54] SUBSTITUTED CROWN POLYETHERS

[75] Inventor: Edmund P. Woo, Midland, Mich.

[73] Assignee: The Dow Chemical Company, Midland, Mich.

[21] Appl. No.: 24,625

[22] Filed: Mar. 28, 1979

[51] Int. Cl.³ .............................................. C08F 8/00
[52] U.S. Cl. .................................. 525/384; 260/338; 525/329; 525/334; 525/385
[58] Field of Search ............... 525/355, 384, 385, 329, 525/334

[56] References Cited

U.S. PATENT DOCUMENTS

| | | | |
|---|---|---|---|
| 3,824,215 | 7/1974 | Takekashi et al. | 525/429 |
| 3,840,606 | 10/1974 | Vanlerberghe | 260/615 B |
| 3,959,390 | 5/1976 | Vanlerberghe | 260/615 R |
| 4,003,961 | 1/1977 | Stevens et al. | 526/321 |
| 4,043,979 | 8/1977 | Cram | 525/385 |
| 4,113,739 | 9/1978 | Trucks et al. | 260/338 |

*Primary Examiner*—Wilbert J. Briggs, Sr.
*Attorney, Agent, or Firm*—Douglas N. Deline

[57] ABSTRACT

Substituted crown polyethers and processes for their manufacture and use are disclosed.

13 Claims, No Drawings

SUBSTITUTED CROWN POLYETHERS

BACKGROUND OF THE INVENTION

Crown polyethers or macrocyclic polyethers are neutral compounds containing 4-20 oxygen atoms each separated from the next by two or more carbon atoms. They have been found to form stable complexes with salts of certain metals and with ammonium salts; "Macrocyclic Polyethers and Their Complexes", C. J. Pederson et al., ANGEW, CHEM. Internat, Edit., Vol. 11, page 16, (1972); and U.S. Pat. Nos. 3,562,295 and 3,687,978. Crown polyethers are believed to form salt-polyether complexes in which the cation is encircled by the oxygen atoms of the polyether ring and is held there by the electrostatic attraction between the cation and the negative ends of the carbon-oxygen dipoles. Since the stereo models of crown polyethers give a crown-like appearance, they are commonly designated as N-crown-M polyethers, wherein N is the total number of atoms in the polyether ring and M is the number of oxygen atoms in the polyether ring.

The crown polyethers ranging in size from cyclic tetramers of ethylene oxide (12-crown-4) and of oxetane (16-crown-4) to 60-membered polyether rings (dibenzo 60-crown-20) have been reported. The most effective complexing agents are said to be found among those polyethers containing 5-10 oxygen atoms each separated from the next by two carbon atoms.

Because of their ability to form complexes with alkali and alkaline earth cations they have been used extensively as phase-transfer catalysts in many organic reactions. However, the application of crown polyethers in industrial processes has been hampered by their toxicity. A further disadvantage is caused by high initial cost and the subsequent inability to recover and recycle the crown polyether because of its solubility in water and other solvents. A need has therefore existed for a crown substituted polyether capable of attaching to a resin or other insoluble inert supportive material. Crown polyether compounds attached to inert supportive materials in this manner are thus prevented from becoming exposed to workers and the environment; and are easily recoverable for reuse.

While crown polyethers are themselves well-known, substituted crown polyethers capable of covalently bonding to inert supportive materials have not been generally produced. Cinouini et al. in *Journal of Chem. Soc., Chem. Commun.*, 394 (1976) described a synthesis of the following alkylamine-substituted crown polyether:

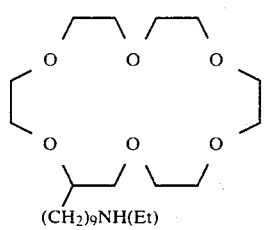

(CH₂)₉NH(Et)

While this substituted crown polyether is capable of bonding to an inert supportive material there are certain disadvantages in its use. First, the molecule will likely attach to a supportive material through formation of an amide or imide. In these cases the bonding will be sensitive to strong alkali, as found under some phase-transfer conditions. Furthermore when attached to a commonly used supportive material such as chloromethylated polystyrene, the bonding will generate secondary amine functionality. The presence of this secondary amine functionality will interfere with the activity of the crown polyether moiety by reacting with acids and itself complexing with metal ions. The amine groups may also interfere if the resin is used in nucleophilic displacement reactions by reacting with the substrate.

It would be desirable to produce a substituted crown polyether capable of attaching to inert supportive materials that does not have the concommitant disadvantages of the prior art.

Other known crown polyether derivatives include benzene derivatives such as:

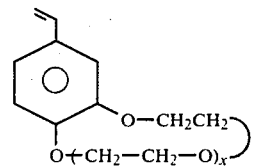

disclosed in Varma, A. J., et al., *J. Poly. Sci., Poly. Chem. Ed.*, 15, 1189 (1977) and:

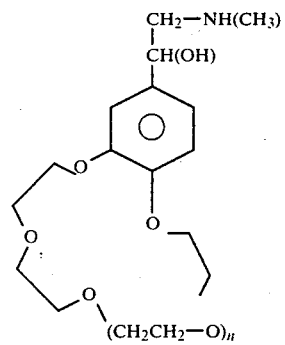

disclosed by VonVögtle, F., et al., *Tetrahedron Letters*, 4895 (1976).

U.S. Pat. No. 4,139,539 to Thomas A. Chamberlin et al., and 4,140,847 to Jon A. Orvik et al., disclose compounds having formulas

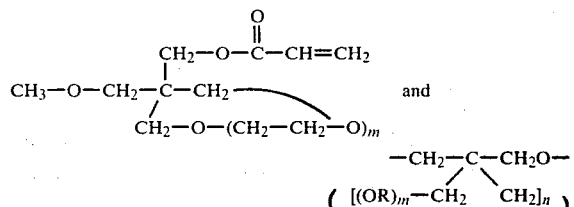

respectively. In both instances the macrocyclic polyether compounds are disubstituted such that both substituents are attached to the same methylene moiety. Furthermore the disubstituted methylene moiety is attached on both sides in the ether ring to other methylene moieties.

BRIEF SUMMARY OF THE INVENTION

The invention comprises new, substituted crown polyether compounds of the formula

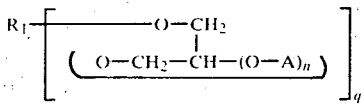

wherein $R_1$ is hydrogen, a hydrocarbon radical or a substituted hydrocarbon radical, including a polymeric hydrocarbon or substituted hydrocarbon radical, or other inert supportive material; A is an alkylene group represented by the formula

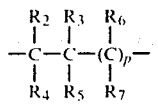

wherein p is zero or 1, $R_2$ to $R_7$ are each occurrence independently hydrogen or radicals having up to 15 carbons taken from a group consisting of alkyl, aryl and arylalkyl; n is 3, 4, 5 or 6; and q is an integer equal to or greater than one.

Preferred in the invention are compounds wherein p equals zero, $R_2$ to $R_5$ are hydrogen and n equals 4 or 5.

One particular embodiment of this invention, the hydroxymethyl crown polyethers, ($R_1$=H) may be converted to various derivatives, such as esters and carbonates. Furthermore, these hydroxymethyl crown polyethers may also be attached to various polymeric substances, such as chloromethylated polystyrene, homopolymers of acrylates and copolymers of acrylates, etc. When so attached the invention may be used as a recoverable phase-transfer catalyst or used in ion-exchange chromatography.

The compounds of this invention may be utilized in processes where heretofore unsubstituted crown polyethers have been used, including uses as phase-transfer catalysts, for example, as nucleophilic substitution reaction catalysts. Other uses for the invention may arise in the generation of carbenes and Wittig reagents, or the polymerization of lactams or other reactions where it is already known that crown polyethers are effective.

A further use of the compounds of this invention is observed when R is a polymerizable radical, for example, $CH_2$=CH—$CH_2$—, or $$CH_2=CH-\overset{O}{\underset{\|}{C}}-.$$

etc. The compounds may then be polymerized to produce substituted crown polyethers wherein crown polyether moieties are permanently incorporated into a polymeric backbone. Both the monomer and the polymer are included within the scope of this invention.

DETAILED DESCRIPTION OF THE INVENTION

The compounds of the invention of Formula I may illustratively be prepared by the following reaction. First, a polymethylene glycol (PMG) of the formula

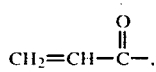

wherein p and $R_2$ to $R_7$ are as defined hereinbefore and x is a positive integer such that x=n−y wherein n is as previously defined and y is as hereinafter defined, is reacted with a tertiary alkyl glycidyl ether (t-AGE) to give a tertiary alkoxymethyl polymethylene glycol. This reaction may be illustrated diagrammatically as

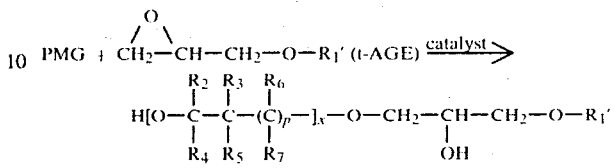

wherein $R_1'$ is a tertiary alkyl radical that serves to protect the oxy bond from attack. Any tertiary alkyl radical is suitable for this purpose. Illustrative of such radicals are tertiary butyl, tertiary amyl, 1-methyl-1-phenylethyl, 1,1-diphenylethyl, etc.

A preferred polymethylene glycol reactant is polyethylene glycol (PEG). A preferred tertiary alkyl glycidyl ether is tertiary butyl glycidyl ether (t-BGE).

A preferred catalyst for this step is $BF_3$-etherate employed in a preferred weight percent concentration of from about 0.5 to about 1 based on the weight of t-AGE used. A solvent may also be employed; for example, dichloromethane. The amount of solvent needed may be selected on the basis of operating convenience based on the particular reactants used.

The reaction is carried out over a wide range of temperatures, conveniently from about 30° C. to about 70° C. with a preferred range from about 40° C. to about 50° C. Generally it is possible to contact the reactants in the PMG:t-AGE molar ratio of from about 1:1 to 10:1. The preferred PMG:t-AGE molar ratio varies from about 2.5:1 to 4:1. The reaction is conveniently carried out at atmospheric pressure, but higher or lower pressure may be employed if desired. The reaction time depending on these various conditions may vary over a range from about 1 to about 24 hours, but generally will require about 3 to about 5 hours.

After reaction is complete the acid catalyst is neutralized with a small quantity of an aqueous solution of alkali hydroxide. The solvent is removed by common techniques such as evaporation and the residue distilled under reduced pressure.

The second step, preparation of tertiary alkoxymethyl crown polyether, involves the Williamson condensation of the tertiary alkoxymethyl polymethylene glycol (Reactant I) with an α,ω-substituted polymethylene ether (Reactant II) of the formula

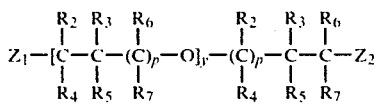

wherein p and $R_2$ to $R_7$ are as hereinbefore defined, and y is a second positive integer related to x such that y=n−x; and $Z_1$, $Z_2$ independently are selected from a group consisting of halogen and

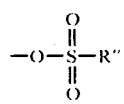

wherein R" is aryl or alkyl. By halogen, halo or halide wherever these expressions occur both in the specification and claims is meant fluorine, chlorine, bromine and iodine. The preferred Reactant II is polyethylene dichloride.

The reaction proceeds in the presence of a base as follows:

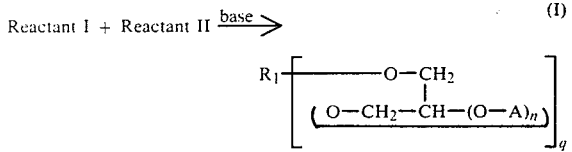

Reactant I + Reactant II $\xrightarrow{\text{base}}$ $$R_1 \left[ \begin{array}{c} -O-CH_2 \\ (O-CH_2-CH-(O-A)_n) \end{array} \right]_q \quad (I)$$

wherein $R_1$ is $R_1'$ and q equals 1.

This reaction is a well-known method of forming cyclic polyethers and may be found in G. W. Gokel et al., J. Org. Chem., 39, 2445 (1973). A wide variety of bases may be used including the alkali and alkaline earth oxides, hydroxides and carbonates, alkali alkoxides and amides, and alkali hydrides. Preferred are alkali hydroxides. The preferred quantity of base is from about 200 to about 300 mole percent of the substituted polyethylene ether used. Alternatively, alkyl metal alkoxides of Reactant I may be preformed from the reaction of Reactant I with the metal and substituted for Reactant I and additional base may be omitted.

The reactants may be combined in a wide range of concentrations, the Reactant I:II molar ratio suitably ranging from about 1:1 to about 3:1. The preferred range is from about 1:1 to about 1.5:1.

Reaction conditions for this second reaction will vary depending on the particular reactants chosen. A wide variety of temperatures may be used; preferably from about 40° C. to about 150° C., and most preferably from about 50° C. to about 75° C. The reaction may require from about 10 hours to about 72 hours or more but usually requires from about 24 to about 48 hours depending on the reaction conditions.

The reaction may be carried out at atmospheric pressure but higher or lower pressures may be utilized if desired. A suitable inert solvent such as tetrahydrofuran may also be employed. The amount of solvent used in this step likewise may be selected on the basis of the operating convenience of the particular reactants employed.

Upon completion of this step of the reaction the product is recovered and purified. The product, tertiary alkoxymethyl crown polyether, comprises one embodiment of the invention.

Another embodiment of the invention is formed by a subsequent step, the dealkylation of the pendant tertiary alkyl group in the presence of an acid. This step results in the production of a hydroxymethyl crown polyether.

It is preferred in this dealkylation step to employ a tertiary alkoxymethyl crown polyether having a tertiary alkyl radical that is a good leaving group. For this purpose tertiary butyl has been found to be a suitable leaving group.

The dealkylation may be accomplished by dissolving the tertiary alkoxymethyl crown polyether in a nonreactive solvent such as toluene, refluxing in the presence of a cation-exchange resin in the hydrogen form, and recovering the dealkylated product. The resin may be employed in concentrations as low as about 0.05 milliequivalents of ion-exchange resin per gram of tertiary alkoxymethyl crown polyether. Preferred is a range from 0.2 to 0.5 milliequivalents of resin per gram of crown polyether.

The refluxing may be carried on over a temperature range from about 90° C. to about 150° C. with a preferred range from about 100° C. to about 110° C. Again it is preferred to operate at atmospheric pressure but higher or lower pressures may be utilized if so desired. The reaction time will vary from as little as about 1 hour up to as long as about 5 hours with a preferred range from about 1 to about 3 hours depending on the reaction conditions selected.

Other means of dealkylation may also be known and employed to produce the dealkylated compounds of the present invention.

Still another embodiment of the present invention is the substituted methyl crown ether wherein $R_1$ is a hydrocarbon radical or substituted hydrocarbon radical. By hydrocarbon radical is meant aliphatic and aromatic radicals. Illustrative hydrocarbon radicals include: alkyl having from 1 to about 15 carbon atoms, alkenyl having from 2 to about 15 carbon atoms, aryl having up to about 15 carbon atoms. $R_1$ may also be arylalkyl, alkylaryl, or alkenylaryl, in each case having up to about 15 carbon atoms.

By substituted hydrocarbon radical is meant an aliphatic or aromatic radical substituted with halogen, cyano, carbonyl, alkoxy and polyether alkoxy substituents.

Several methods exist for preparing the compounds of this embodiment of the invention. For example, a hydroxymethyl crown polyether may conveniently be condensed with a halogen substituted hydrocarbon in the presence of a base. Alternatively a standard Williamson synthesis may be employed. Utilizing these processes it may be seen that a wide variety of hydrocarbon radicals and substituted hydrocarbon radicals may suitably be incorporated into the compounds. When using the Williamson-type synthesis one halogen is eliminated from the halogen substituted hydrocarbon reactant. Therefore dihalogenated or multihalogenated hydrocarbon reactants must be utilized to produce monohalogenated or multihalogenated hydrocarbon radicals in the finished substituted polyether. Further substituents that do not interfere with the Williamson synthesis may also be present in the halogen substituted hydrocarbon reactant.

When employing aryl, alkylaryl, and alkenyl compounds in the Williamson-type condensation it is advantageous to employ a catalyst such as copper metal or a copper salt in order to promote the formation of the ether compound.

Another means of incorporating hydrocarbon radicals into the compounds is by reacting the hydroxymethyl substituted crown polyether with an alkyl oxide in the presence of either an acidc or basic catalyst. The resulting product is the corresponding methyl crown polyether polymethylene glycol wherein $R_1$ is equal to $[CH_2-CH_2-(CH_2)_k-O]_mH$; andk is an integer equal to zero, 1, 2, or 3 and m is 1, 2, 3, 4 or 5. For example, $R_1$ may be $-CH_2-CH_2-OH$, $CH_2-CH_2-CH_2-OH$, $-CH_2-CH_2-O-CH_2-CH_2-OH$, etc.

It is also possible to contact the hydroxymethyl crown polyether with a compound such as acrylonitrile. Addition across the double bond occurs producing the corresponding substituted crown polyether compound wherein $R_1$ is a cyanoalkyl radical. 2-cyanoethoxy substituted methyl crown polyethers are illustrative of these compounds.

The hydroxymethyl crown polyether also may be subjected to transesterification by, for example, contacting under appropriate conditions with carbonyl containing compounds in the presence of an acid catalyst. The process results in the formation of substituted polyethers having carbonyl functionality in the substituent.

In another embodiment of this invention the hydroxymethyl substituted compounds are conveniently attached to inert supportive materials. Several means of attachment are possible including physical entrapment onto the surface of an inert support as is taught for instance by U.S. Pat. No. 4,140,847; which teaching is herein incorporated by reference.

Alternately the polyether moiety may become chemically bonded to an inert supportive material as for example by covalent bonding. In this embodiment $R_1$ of Formula I is the inert supportive material. Preferred supportive materials for covalent bonding include polymeric resin compositions such as halomethylated polystyrene, or other polymeric compounds containing reactive halogen substituents, homopolymers of acrylates, and copolymers containing acrylate functionality. A most preferred supportive material for covalently bonding of the hydroxymethyl substituted compounds is chloromethylated polystyrene.

For ease of handling, the polymeric resin compositions may be in the form of beads or other convenient shape. When beads are employed the bead size is not critical. Generally bead sizes measured according to the U.S. standard series of screen size ranging from 16–10 mesh or larger to 200–400 mesh or smaller are all acceptable.

Attachment of the hydroxymethyl crown polyether to, for example, halomethylated polystyrene by covalent bonding may be occasioned by a Williamson condensation similar to the process for forming the tertiary alkoxymethyl crown polyethers described earlier. First the alkoxide of the hydroxymethyl crown polyether is formed by treating the hydroxymethyl substituted crown ether with an alkali hydride or alkali hydroxide in an inert solvent suitably chosen to dissolve the alkoxide reaction product. Examples of suitable solvents include a mixture of toluene and dioxane, dimethyl formamide, other amide-containing solvents, dimethyl sulfoxide, alkylated polyethers, etc. A preferred solvent is a mixture of toluene and dioxane.

Next, a portion of cross-linked halomethylated polystyrene is added to the alkoxide solution and the mixture refluxed for a sufficiently long time period to allow the hydroxymethyl crown ether to attach to the polystyrene support. The amount of time allowed for refluxing is not critical but must be sufficient to permit a significant amount of alkoxide to penetrate into the interior of the halomethylated polystyrene matrix and bond to the polystyrene. Depending on the amount of bonding desired it may be necessary to continue refluxing from several hours to as long as 48 hours or more.

The amount of halomethylation present in the original resin may vary over a wide range. No known reason exists to limit the maximum degree of halomethylation present while likewise no known reason exists to limit the minimum degree of halomethylation present, excepting that smaller degrees of halomethylation will of course result in a resin containing less crown ether functionality. Practically, cross-linked polystyrene resin containing as little as 0.1 meq halogen per gram of resin as measured by titration according to the Volhard procedure may be utilized.

After the alkoxide reaction is discontinued some halomethyl functionality may remain in the finished resin due to incomplete reaction with the alkoxide. In this instance the polymeric resin supportive material consists of a mixture of cross-linked polystyrene and cross-linked halomethylated polystyrene. Since the supportive material may be such a mixture the amount of halomethylated polystyrene resin added to the alkoxide solution is not critical. It is preferred, however, to add about an equal number of equivalents of alkoxide and resin determined by the degree of halogenation present in the resin.

After refluxing is completed the polystyrene having monosubstituted crown polyether compounds covalently bonded thereto is separated from the reaction mass, as for example by filtration, washed with inert solvents, and dried.

When homopolymers of acrylate and copolymers containing acrylate functionality, or other inert supportive materials to which the hydroxymethyl substituted crown polyethers are capable of attaching are utilized, it may be necessary to attach the substituted crown polyethers by other means. Accordingly, by the process of transesterification, one may produce the desired product, for example, when reacting a polymer of methyl acrylate with the hydroxymethyl substituted crown polyether in the presence of an acid catalyst. Similarly, if one reacts a copolymer containing acrylic acid with the hydroxymethyl substituted crown polyethers in the presence of an acid catalyst the desired ester linkage is formed. Other means for attaching substituted crown polyethers to inert supportive materials such as physically trapping of the molecule in the pores of a porous support as disclosed in U.S. Pat. No. 4,140,847, will be known to those skilled in the art.

When polymeric resin compositions are employed as the inert supportive material in this invention, they preferably contain internal cross-linkages formed advantageously according to methods employed heretofore in the preparation of ion-exchange resins. For example, said cross-linkages may be formed as a result of a copolymerization with known cross-linking agents such as polyvinylidene aromatic polyethylenically unsaturated monomers, including: divinylbenzene, divinyltoluene, divinylxylene, divinylnaphthalene, etc. Other methods of forming cross-linkages in the polymeric resin supportive materials employed in this invention will be well-known to those skilled in the art.

The amount of cross-linking present in the polymer may affect the invention in that the degree of cross-linking controls the porosity of the resin thus affecting the rate of attachment of hydroxymethyl substituted crown ethers to the polymeric resin. The amount of porosity also affects the later performance of the invention in, for example, its use as a phase-transfer catalyst, by affecting the ability of cationic reaction species to permeate the resin structure. Preferred cross-linkage percentages may vary from about 0.5 percent to about 20 percent and most preferably they vary from about 1 percent to about 10 percent as measured advantageously by the percentage of cross-linking comonomer added during the production of the polymeric resin.

Once the substituted crown polyether compounds are attached to an inert supportive material, the completed composition may be used in a variety of applications, including generally, those applications known to the prior art wherein, heretofore, crown polyethers have been advantageously employed. The effect of the invention and likewise that of known crown polyethers is thought to be due to the ability to form complexes with salts, specifically with the cationic species.

In nucleophilic substitution reactions the invention whether in the embodiment wherein the substituted crown polyether compound is bound to inert supports or not so bound to inert supports is added in a catalytically effective amount, preferably at least about 0.5 mole percent based on the cationic species to be complexed. The invention in all embodiments may advantageously be employed in nucleophilic substitution reactions at elevated temperatures if desired. It is preferred however to employ substituted crown polyethers bound to inert supports at temperatures less than the upper limit of thermal stability of the inert supportive material employed, which in the case of the commonly used polystyrene divinylbenzene supportive material may be as high as about 150° C. or even higher.

SPECIFIC EMBODIMENTS OF THE INVENTION

The following examples are illustrative of the compounds and processes of the present invention.

EXAMPLE 1

Preparation of t-butoxymethyl triethylene glycol

A solution of 100 g (0.77 mole) t-BGE in 100 ml dichloromethane was slowly added with stirring to a glass round bottom flask containing a solution of 250 g (2.4 moles) diethylene glycol and 0.5 ml boron trifluoride etherate catalyst in 150 ml dichloromethane that had first been preheated to 36° C. Over the course of addition (approximately 1.25 hr) the reaction temperature rose to about 45° C. and the dichloromethane began to reflux. The reaction was continued with stirring for about 2 hours after completion of t-BGE addition. A small quantity, approximately 1 g of sodium hydroxide and 20 ml of water were added to the reaction vessel contents. The solvent was then removed by evaporation and the product residue distilled at 0.7 mm Hg pressure. Tertiary butoxymethyl triethylene glycol (71 g, 39 percent yield) was recovered having a boiling point range from 139°–145° C. Analysis by nuclear magnetic resonance (NMR) and infrared (IR) absorption spectroscopy confirmed the product's identity.

Preparation of t-butoxymethyl-18-crown-6-polyether

To a solution of tertiary butoxymethyl triethylene glycol (59 g, 0.25 mole) in 125 ml tetrahydrofuran contained in a glass round bottom flask was added a solution of potassium hydroxide (36.25 g) in 20 ml of water. After stirring with a magnetic stirrer for 5 min. a solution of triethylene glycol dichloride (46.8 g, 0.25 mole) in 25 ml tetrahydrofuran was added and the mixture refluxed for 24 hours. The solution was filtered to remove the potassium chloride by-product. Evaporation of solvent left a viscous oil which upon distillation at 0.7 mm Hg yielded 16 g (18 percent yield) of a viscous liquid (b.p. 165° C.–167° C.) identified by NMR and IR spectroscopy as t-butoxymethyl-18-crown-6 polyether ($R_2$—$R_5$=H, p=0, n=5, q=1).

EXAMPLE 2

Dealkylation of t-butoxymethyl-18-crown-6 polyether

Five grams of tertiary butoxymethyl-18-crown-6 polyether produced in Example 1 was dissolved in 50 ml toluene and refluxed in a glass round bottom flask for 2 hours with 0.4 g of DOWEX brand MSC-1 cation-exchange resin in the H$^\oplus$ form, a strong acid macroporous resin made by nuclear sulfonation of a styrene/divinylbenzene copolymer. The reaction vessel contents were filtered to remove the resin. After solvent removal by evaporation, 4 g of a colorless oil remained. Analysis by NMR and IR spectroscopy and by gas chromatography identified the oil as substantially pure hydroxymethyl-18-crown-6 polyether.

EXAMPLE 3

Preparation of t-butoxymethyl diethylene glycol

To a solution of ethylene glycol (248 g, 4 moles) and boron trifluoride etherate catalyst (1 ml) in dichloromethane (20 ml) preheated to 45° C. was added t-BGE (130 g, 1 mole) dropwise at such a rate so as to maintain a gentle reflux. After completion of addition, stirring was continued for about 15 hours. The solution was then adjusted to pH 7.5 by addition of sodium hydroxide and the product removed by distillation. Tertiary butoxymethyl diethylene glycol was obtained in 71 percent yield having a boiling point of 105° C.–115° C./1 mm.

Preparation of t-butoxymethyl-15-crown-5 polyether t-Butoxymethyl diethylene glycol (38.4 g, 0.2 moles) and triethylene glycol dichloride (37.6 g, 0.2 mole) were added dropwise over 1 hour to a slurry of sodium hydride (25 g of 50 percent dispersion) in 250 ml of tetrahydrofuran. The reaction mass was refluxed for about 48 hours and the resulting solution filtered. A 13 g portion boiling at 115° C.–140° C. consisting of about 25 percent unreacted glycol and about 75 percent crown polyether resulted from distillation of the filtrate at 0.5 mm Hg. Purification by absorption of glycol on an alumina column left t-butoxymethyl-15-crown-5 polyether ($R_2$-$R_5$=H, p=0, n=4, q=1), boiling at 127° C.–130° C./0.3 mm in 8 percent yield.

EXAMPLE 4

Dealkylation of t-butoxymethyl-15-crown-5 polyether

A small quantity of t-butoxymethyl-15-crown-5 polyether produced in Example 3 was dealkylated by refluxing with ion exchange resin as in Example 2. Analysis by NMR and IR spectroscopy confirmed the formation of hydroxymethyl-15-crown-5 polyether.

EXAMPLE 5

Polystyrene bound 18-crown-6 polyether

A small portion (6.2 g, 0.021 mole) of hydroxymethyl 18-crown-6 polyether produced according to Example 2 above was dissolved in 100 ml toluene and 150 ml dioxane in a glass round bottom flask. Sodium hydride (3 g of 50 percent oil dispersion) was added along with 15 g of 2 percent cross-linked chloromethylated polystyrene beads (1.19 meq of Cl/g beads). This admixture was refluxed for 48 hours. The polystyrene beads were removed by filtration and washed in succession with toluene, methanol, water and again with methanol. Yield after drying in vacuo was 19.0 or 97 percent. Titration according to the Volhard procedure indicated less than 5 percent hydrolyzable chloride remained, corresponding to 0.85 meq of crown polyether per gram of beads.

EXAMPLE 6

Polystyrene-bound crown polyether as phase-transfer catalyst

A portion (1.2 g, 1.0 meq) of the polystyrene beads prepared in Example 5 above was refluxed with a mixture of n-octyl bromide (4 g, 0.02 mole), potassium cyanide (3.25 g, 0.05 mole), toluene (10 ml) and water (6.5 ml). The yield of n-octyl cyanide was determined by gas chromatography to be 28.5 percent after 1 hour, 34 percent after 1.5 hour, and 48 percent after 2 hours.

By way of contrast, a similar experiment was conducted using the above reactants in the absence of polystyrene bound hydroxymethyl crown polyether beads of Example 5. After reaction for 2 hours no detectable amount of n-octyl cyanide was found.

What is claimed is:

1. A substituted crown polyether of the formula

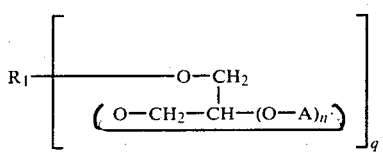

wherein
(1) $R_1$ is a polymeric radical selected from reactive halogen containing polymers, homopolymers of acrylates, and copolymers containing acrylate functionality;
(2) A is an alkylene group represented by the formula

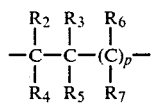

wherein p is zero or 1, $R_2$ to $R_7$ are each occurrence independently hydrogen or radicals having up to 15 carbons taken from a group consisting of alkyl, aryl and arylalkyl;
(3) n is 3, 4, 5 or 6; and
(4) q is an integer greater than or equal to one.

2. A substituted crown polyether according to claim 1 formed by covalently bonding a hydroxymethyl crown ether reactant of the formula

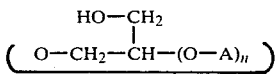

wherein A is an alkylene group represented by the formula

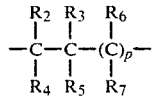

wherein p is zero or 1, $R_2$ to $R_7$ are each occurrence independently hydrogen or radicals having up to 15 carbons taken from a group consisting of alkyl, aryl, and arylalkyl, and n is 3, 4, 5 or 6, to a polymeric resin selected from a group consisting of cross-linked chloromethylated polystyrene, homopolymers of acrylates and copolymers of acrylates.

3. The substituted crown polyether according to claim 2 wherein A of the hydroxymethyl crown ether reactant is —$CH_2$—$CH_2$—.

4. The substituted crown polyether according to claim 2 wherein the hydroxymethyl crown ether reactant is covalently bonded to cross-linked, chloromethylated polystyrene beads.

5. The substituted crown polyether according to claim 4 wherein the cross-linked, chloromethylated polystyrene beads may vary in size from about American Standard mesh size 400 to about American Standard mesh size 16, being cross-linked from about 1 percent to about 10 percent and containing at least 0.1 meq of chlorine per gram of beads.

6. The substituted crown polyether according to claim 4 wherein the hydroxymethyl crown ether reactant is hydroxymethyl 18-crown-6 polyether.

7. In a nucleophilic substitution reaction process whereby a phase-transfer catalyst is utilized, the improvement wherein the phase-transfer catalyst is a substituted crown polyether of claim 1.

8. The process according to claim 7 wherein p is zero, and $R_2$ to $R_7$ are hydrogen.

9. The process according to claim 8 wherein the substituted crown ether phase-transfer catalyst is formed by covalently bonding hydroxymethyl 18-crown-6 polyether to a polymeric resin selected from a group consisting of cross-linked, chloromethylated polystyrene, homopolymers of acrylates, and copolymers of acrylates.

10. The process according to claim 9 wherein the polymeric resin is cross-linked, chloromethylated polystyrene beads.

11. The process according to claim 10 wherein the cross-linked, chloromethylated polystyrene beads may vary in size from about American Standard mesh size 400 to about American Standard mesh size 16, being cross-linked from about 1 percent to about 10 percent and containing at least 0.1 meq of chlorine per gram of beads.

12. The improved nucleophilic substitution process according to claim 10 wherein the reaction process is conducted at temperatures up to about 150° C.

13. A process for covalently bonding hydroxymethyl substituted crown ether compounds to cross-linked chloromethylated polystyrene beads comprising mixing hydroxymethyl substituted crown ether compounds of the formula

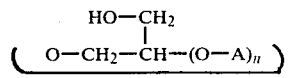

wherein A is an alkylene group represented by the formula

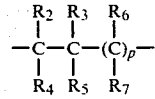

wherein p is zero or 1, $R_2$ to $R_7$ are each occurrence independently hydrogen or radicals having up to 15 carbons taken from a group consisting of alkyl, aryl, and arylalkyl; and n is 3, 4, 5 or 6, with an alkali metal hydride in an inert organic solvent selected from a group consisting of dimethyl formamide, dimethyl sulfoxide, alkylated polyethers, and a mixture of toluene and dioxane; adding cross-linked chloromethylated polystyrene; refluxing the mixture at an elevated temperature; and recovering the resulting product.

* * * * *

UNITED STATES PATENT AND TRADEMARK OFFICE
CERTIFICATE OF CORRECTION

PATENT NO. : 4,256,859
DATED : March 17, 1981
INVENTOR(S) : Edmund P. Woo

It is certified that error appears in the above—identified patent and that said Letters Patent is hereby corrected as shown below:

Col. 2, line 7, "groups" should read --group--.

Col. 6, line 56, "alkyl" should read --alkylene--.

Col. 6, line 57, "acidc" should read --acidic--.

Col. 6, line 60, "andk" should read --and k--.

Col. 10, line 64, add --g-- after "19.0".

Signed and Sealed this

Twenty-ninth Day of September 1981

[SEAL]

Attest:

Attesting Officer

GERALD J. MOSSINGHOFF

Commissioner of Patents and Trademarks